United States Patent [19]

Zakomyrdin et al.

[11] Patent Number: 4,731,240

[45] Date of Patent: Mar. 15, 1988

[54] PREPARATION FOR PROPHYLAXIS AND TREATMENT OF MYIASES OF ANIMALS

[76] Inventors: Alexandr A. Zakomyrdin, Bolshoi Rogozhsky pereulok, IO, korpus I, kv. I27; Mark A. Simetsky, Teply Stan, 4 mikroraion, 45, kv. I36, both of, Moscow; Elena I. Pilipets, prospekt Pravdy, 64, kv. I49, Kiev; Vladimir M. Repin, ulitsa Polimernaya, 7, kv. 49, Moscow; Vitaly I. Ilyaschenko, ulitsa Dorozhnaya, 75, kv. 3, Kustanai; Dmitry G. Klientovsky, Preobrazhensky val, 39, kv. I8, Moscow; Ljudmila I. Golik, Almalyk, ulitsa Navoi, 7, kv. I35; Viktor A. Samkin, Almalyk, ulitsa Lenina, 42, both of, Tashkentskaya oblast; Nina P. Kuznetsova, Zheleznodorozhny, ulitsa Novaya, 5, kv. 32, Moskovskaya oblast, all of U.S.S.R.

[21] Appl. No.: 870,789

[22] Filed: Jun. 5, 1986

[51] Int. Cl.$^4$ ............................................. C07C 19/02

[52] U.S. Cl. ....................................... 424/45; 514/129; 514/141; 514/143; 424/DIG. 10; 424/78; 424/82

[58] Field of Search ................... 424/45, DIG. 10, 78, 424/82; 514/129, 141, 143

[56] References Cited

U.S. PATENT DOCUMENTS

| | | | |
|---|---|---|---|
| 3,966,921 | 6/1976 | Beriger et al. | 424/211 |
| 3,991,213 | 11/1976 | Mitsubayashi | 424/186 |
| 4,035,488 | 7/1977 | Drabek et al. | 424/212 |

*Primary Examiner*—Joseph L. Schofer
*Assistant Examiner*—Angela L. Fugo
*Attorney, Agent, or Firm*—Ladas & Parry

[57] ABSTRACT

The present invention relates to the art of veterinary science. The preparation for prevention and treatment of myiases of animals comprises the following components, percent by mass:

an insecticide exhibiting a larvicidal effect: 1.4 to 2.3 a 5–10% ethanolic solution of polyvinylbutyral and a resol-type phenolformaldehyde resin taken in a ratio of 1:10–45: 16 to 35.0 a plastifying agent improving elasticity of the resulting polymeric film: 1.0 to 20.0 an antibiotic: 0.1 to 0.7 an organic solvent: the balance.

8 Claims, No Drawings

PREPARATION FOR PROPHYLAXIS AND TREATMENT OF MYIASES OF ANIMALS

FIELD OF THE INVENTION

The present invention relates to the veterenary and, more specifically, to a preparation for prophylaxis and treatment of myiases of animals.

BACKGROUND OF THE INVENTION

Myiases—(wound worm-infesting) is a disease of animals caused by larvae of flies of the families Calliphoridae, Sacrophagidae, Muscidae which damage the animals' skin, subcutaneous cellular tissue and underlying muscles. Most frequently injured by myiases are animals having wounds, but myiases can also be originated under the cover of a fleece wool on both healthy and macerated skin of sheep.

For the control of myiases of animals methods of mass treatment of animals are used such as dipping or spraying with solutions of insectidides possessing larvicidal effect.

Known in the art is the use of such insecticides as chlorophos (Divon, Dilox, Trichlorophen), i.e.—O,O-dimethyl-(2,2,2-trichloro-1-oxyethyl)phosphonate or O,O-dimethyl-O-[1-methyl-2-(phenylcarboethoxy)vinyl]-phosphate (Ziodrin) in the form of aqueous solutions for the treatment of myiasis wounds. (Cf. Handbook on Pesticides, Moscow, "Khimiya" Publishers, 1985). However, upon application of these preparations on wounds the required effect is not exerted, the protective action takes place only for 3–5 days necessitating a two-three times' application of these preparation to ensure a complete recovery. Upon administration of these preparations diluted with river or well water the wound infesting is quite possible which instead of curing may result even in aggravation of inflammatory processes. The application of these prior art preparation is labour-consuming, requires rather long time and does not always ensure a desired healing effect. Furthermore, the application of these preparations on animals by way of dipping or spraying is accompanied by high rates of the preparation consumption. In doing so, the preparation is resorbed through the animals' skin and accumulated in the animal's body, thus lowering the sanitary quality of the food products from such animals.

SUMMARY OF THE INVENTION

It is an object of the present invention to provide a preparation for prophylaxis and treatment of myiases of animals which would feature a high efficiency of action, would cause no toxicosis or an irritation effect in animals, suitable for application under any conditions and liable to be stored for a long time.

This object is accomplished by that the preparation for prophylaxis and treatment of myiases of animals according to the present invention incorporating an insecticide possessing a larvicidal effect consists of the following components, percent by mass:
insecticide possessing a larvicidal effect: 1.4 to 2.3
5–20% solution of polyvinylbutyral and resol-type phenolformaldehyde resin in a ratio of 1:(10–45) in ethanol: 16.0 to 35.0
plastifier increasing elasticity of the resulting polymeric film: 1.0 to 20.0
antibiotic: 0.1 to 0.7
organic solvent: the balance.

To enhance the effectiveness of action of the preparation according to the present invention, it preferably incorporates, as the insecticide possessing a larvicidal effect, O,O-dimethyl-O-[1-methyl-2-(phenylcarboethoxin)vinyl]phosphate or O,O-dimethyl-(2,2,2-trichloro-1-oxyethyl)-phosphonate.

As the plastifying agent increasing elasticity of the resulting polymeric film, the preparation according to the present invention preferably contains castor oil or birch tar. These plastifiers contribute to a more uniform coating of the wound surface ensuring rescription of the active principle in the injured tissues simultaneously with depositing them on the wound surface in a film form which is necessary for a normal healing of the wounds. In order to eliminate the development of a pyogenic microflora, the preparation according to the present invention contains an antibiotic, preferably erythromycin. As the organic solvent the preparation according to the present invention preferably contains ethylacetate, ethanol or isopropanol. For convenience of application of the preparation according to the present invention under any conditions, convenience of dispensing, transportation and storage, the preparation according to the present invention can incorporate a propellant in an amount of 10 to 40% by mass. It is preferable that as the propellant the preparation according to the present invention contain difluorodichloromethane or a mixture thereof with propane-butane. In order to ensure an antiinflammatory effect, the preparation according to the present invention can incorporate prednizone in an amount of 0.02 to 0.04% by mass. The preparation according to the present invention makes it possible to kill larvae of myiasis flies in invaded wounds, to prevent a repeated laying of larvae till a complete healing of wounds, to prevent laying fly larvae into frest wounds and accelerate healing of infected wounds, as well as to prevent complications and stop bleeding upon a single-time application of the preparation.

DETAILED DESCRIPTION OF THE INVENTION

The preparation according to the present invention incorporates an isecticide possessing a larvicidal effect in an amount of 1.4 to 2.3% by mass. This amount ensures efficiency of action of the insecticide without causing toxicoses in this concentration. An amount of the insecticide below 1.4% by mass does not provide for the required effect, whereas amounts exceeding 2.3% by mass cause irritation of fresh wounds and provide a detrimental effect on the quality of the amimal products.

Upon application of the preparation according to the present invention on fresh wounds the insecticide, while being under a film, prevents larvae laying by myiasis flies.

The preparation according to the present invention incorporates a film-forming component—a 5–20% solution (in ethanol) of polyvinylbutyral and a resol-type phenolformaldehyde resin taken in a ratio of 1: (10–45) in an amount of from 16 to 35% by mass. This contributes to the formation of an elastic film on the surface of a wound already 1–2 minutes after application of the preparation according to the present invention; this film is resistant to moisture and mechanical factors, it prevents a repeated laying of larvae into the wounds, prevents contamination of the wounds during 8–10 days till a complete healing thereof. The film also prevents penetration of urina, excrements, mud into the wounds; it also protects the wounds from contamination during water-drinking from rivers, springs and the like.

The preparation according to the present invention also incorporates a plastifying agent which improves elasticity of the formed film. As the plastifying agent the preparation according to the present invention may include any suitable plastifiers such as castor oil, dibutylphthalate, cetyl alcohol, birch tar. It is preferred that the preparation according to the present invention contain castor oil and birch tar as the plastifying agent. Plastifiers contribute to a uniform coating of the wound surface which ensures restorption of the active principle in the injured tissues and an accelerated healing of the wounds.

An antibiotic is also incorporated into the fomulation of the preparation according to the present invention. As the antibiotic, the preparation of this invention may incorporate any acceptable antibiotic of a broad-spectrum action such as tetracyclin and derivatives thereof, streptomycin, erythromycin; erythromycin being preferable.

The incorporation of an antibiotic into the preparation's formulation ensures a total inactivation of a pyogenic microflora. The incorporation of prednizone in an amount of 0.02 to 0.04% by mass into the preparation according to the present invention provides an antiinflammatory effect thereof.

The preparation according to the present invention also includes an organic solvent which can represent any suitable non-toxic solvent such as ethanol, butanol, isopropanol, ethylacetate or hexane.

The preparation according to the present invention can be applied onto the wound surface by different methods. In order to ensure a fuller covering of the wound surface and edges of non-injured zones, as well as to provide an all-round contact of the active principle with the wound surface, the preparation according to the present invention is applied as an aerosol foam. As the propellant contributing to the foaming on the wound surface use is preferably made of difluorochloromethane or a mixture thereof with propanebutane. The foam is applied onto the wound surface without removing larvae and trying to extend its edges so that foam penetrates into all cavities and pockets. The foam provides an irritating effect on larvae, coats their spiracles and causes their overincreased activity. Coming into an excited state the larvae leave the wound. Their death comes 1–1.5 hours after the treatment. Sometimes the first-age larvae that left the sites of their parasitism, but not fallen out remain in the wound. They are coated with the film and die but do not degrade due to the presence of bacteriostatic substances. Mummified larvae are rejected from the wound surface together with the film within 7 to 15 days after the treatment. In the case of considerable a amounts of a necrotic mass in the wound the foam treatment can be repeated so to provide more favourable conditions for healing. The preparation according to the present invention has been tested on 1.5 mln head of small cattle and 10,000 head of cattle. The preparation was applied locally onto the surface of wounds injured with myiases and into fresh wounds for prophylaxis of laying larvae. The preparation was administered as an aerosol foam. Within 1–5 minutes on the wound surface an elastic film coating was formed which remained intact till a complete healing of the wound (7 to 10 days). A visual observation showed that after 1, 3, 5, 7, 9 and 12 days the film coating was not broken and fully protected the wounds from a repeated invasion of myiasic flies larvae. There was noted no irritation effect of the preparation on the wound tissues, or signs of toxicoses in the treated animals. The preparation according to the present invention suppresses the growth of microflora in wounds, slows down the inflammatory processes, contributes to regeneration of the injured tissues and to healing of wounds within a period of from 7 to 10 days.

The preparation according to the present invention is obtained by intermixing the starting components in the above-specified proportions, followed by dissolution thereof in an organic solvent.

The preparation according to the present invention retains activity for a long storage periods of up to 2 years.

For a better understanding of the present invention some specific examples are given hereinbelow, illustrating particular embodiments of the preparation and tests thereof.

EXAMPLE 1

A preparation of the following composition is formulated, % by mass:
0,0-dimethyl-0-[1-methyl-2-(phenylcarboethoxin)-vinyl]phosphate: 1.4
castor oil: 1.0
5% solution of polyvinylbutyral and resol-type phenolformaldehyde resin (in the ratio of 1:10) in ethanol: 16.0
erythromycin: 0.1
ethanol: the balance.

The components are intermixed in the above-specified amounts and dissolved in ethanol. The preparation according to the present invention is applied onto the site of the myiatic injury of sheep skin (10 heads) and cattle (5 heads). For the purposes of control a single-time and two-times dipping of the same number of animals is effected with 1% solution of O,O-dimethyl-(2,2,2-trichloro-1-oxyethyl)phosphonate. In the wounds treated with the preparation according to the present invention larvae of myiasis flies come into an excited state, start randomly moving around and fall out of the wound. Within 1–2 minutes after application of the preparation according to the present invention an elastic water-resistant and vapour-permeable film is formed on the wound surface. The control of the state of wound surfaces in the animals of the test and control groups is effected for 15 days with a day's interval between observations.

The test results are given in the Table hereinbelow.

EXAMPLE 2

A preparation of the following composition is formulated, % by mass:
0,0-dimethyl-0-[1-methyl-2(phenylcarboethoxin)-vinyl]-phosphate: 2.0
castor oil: 10.0
5% solution (in ethanol) of polyvinylbutyral and resol-type phenolformaldehyde resin (in the ratio of 1:20): 25.0
erythromycin: 0.1
ethanol: the balance.

The formulation and testing of the preparation are carried out in a manner similar to that described in the foregoing Example 1. The test results are shown in the Table hereinbelow

EXAMPLE 3

A preparation according to the present invention of the following composition, % by mass, is formulated:
0,0-dimethyl-0-[1-methyl-2(phenylcarboethoxin)vinyl]-phosphate: 2.3
castor oil: 20.0
5% solution (in ethanol) of polyvinylbutyral and resol-type pnenolformaldehyde resin (in the ratio of 1:45): 35.0
erythromycin: 0.7
ethanol: the balance.

The production and testing of the preparation are carried out in a manner similar to that of Example 1 hereinbefore. The test results are shown in the Table hereinbelow.

EXAMPLE 4

A preparation according to the present invention having the following composition, % by mass, is formulated:
0,0-dimethyl-0-[1-methyl-2(phenylcarboethoxin)-vinyl]phosphate: 1.4
birch tar: 1.0
5% solution (in ethanol) of polyvinylbutyral and resol-type phenolformaldehyde resin (in the ratio of 1:20): 16.0
erythromycin: 0.1
ethanol: the balance.

The manufacture and testing of the preparation are carried out as described in Example 1. The results of the tests are shown in the Table hereinbelow.

EXAMPLE 5

A preparation according to the present invention having the following composition, % by mass, is formulated:
0,0-dimethyl-0-[1-methyl-2(phenylcarboethoxin)vinyl]-phosphate: 2.0
birch tar: 10.0
5% solution (in ethanol) of polyvinylbutyral and resol-type phenolformaldehyde resin (in the ratio of 1:20): 25.0
erythromycin: 0.4
ethanol: the balance.

The manufacture and testing of the resulting preparation are carried out as described in the foregoing Example 1. The test results are shown in the Table hereinbelow.

EXAMPLE 6

A preparation according to the present invention having the following composition, % by mass, is formulated:
0,0-dimethyl-0-[1-methyl2(phenylcarboethoxin)vinyl]-phosphate: 2.3
birch tar: 20.0
10% solution (in ethanol) of polyvinylbutyral and resol-type phenolformaldehyde resin (in the ratio of 1:20): 35.0
erythromycin: 0.7
ethanol: the balance.

The manufacture and testing of the resulting preparation are carried out in a manner similar to that described in Example 1 hereinbefore. The results of the tests are shown in the Table hereinbelow.

EXAMPLE 7

A preparation according to the present invention having the following composition, % by mass, is formulated:
0,0-dimethyl-0-[1-methyl2(phenylcarboethoxin)vinyl]-phosphate: 1.4
cetyl alcohol: 1.0
20% solution (in ethanol) of polyvinylbutyral and resol-type phenolformaldehyde resin (in the ratio of 1:20): 16.0
erythromycin: 0.1
ethanol: the balance.

The manufacture and testing of the resulting preparation are conducted following the procedure described in Example 1. The test results are shown in the Table hereinbelow.

EXAMPLE 8

A preparation according to the present invention having the following composition, % by mass, is formulated:
0,0-dimethyl-0-[1-methyl-2-(phenylcarboethoxin)-vinyl]-phosphate: 2.0
dibutylphthalate: 10.0
5% solution of polyvinylbutyral and resol-type phenolformaldehyde resin (in the ratio of 1:20) in ethanol: 25.0
erythromycin: 0.4
ethanol: the balance.

The manufacture and testing of the preparation are carried out in a manner similar to that of Example 1. The test results are shown in the Table hereinbelow.

EXAMPLE 9

A preparation according to the present invention having the following composition, % by mass, is formulated:
0,0-dimethyl-(2,2,2-trichloro-1-oxyethyl)phosphonate: 1.4
castor oil: 1.0
5% solution of polyvinylbutyral and resol-type phenolformaldehyde resin (in the ratio of 1:20) in ethanol: 16.0
erythromycin: 0.1
ethanol: the balance.

The manufacture and testing of the resulting preparation are carried out in a manner similar to that described in Example 1. The test results are shown in the Table hereinbelow.

EXAMPLE 10

A preparation according to the present invention having the following composition, % by mass, is formulated:
0,0-dimethyl-(2,2,2-trichloro-1-oxyethyl)phosphonate: 2.0
castor oil: 10.0
10% solution of polyvinylbutyral and resol-type phenolformaldehyde resin (in the ratio of 1:20) in ethanol: 25.0
erythromycin: 0.4
ethanol: the balance.

The manufacture and testing of the resulting preparation are carried out following the procedure described in Example 1. The test results are shown in the Table hereinbelow.

EXAMPLE 11

A preparation according to the present invention having the following composition, % by mass, is formulated:

0,0-dimethyl-(2,2,2-trichloro-1-oxyethyl)phosphonate: 2.3
castor oil: 20.0
5% solution of polyvinylbutyral and resol-type phenol-formaldehyde resin (in the ratio of 1:20) in ethanol: 35.0
erythromycin: 0.7
ethanol: the balance.

The manufacture and testing of the produced preparation are carried out similarly to those described in Example 1. The test results are shown in the Table hereinbelow.

EXAMPLE 12

A preparation according to the present invention having the following composition, % by mass, is formulated:

0,0-dimethyl-(2,2,2-trichloro-1-oxyethyl)phosphonate: 2.0
birch tar: 10.0
10% solution of polyvinylbutyral and resol-type phenolformaldehyde resin (in the ratio of 1:20) in ethanol: 25.0
erythromycin: 0.4
ethanol: the balance.

The manufacture and testing of the resulting preparation are carried out as described in Example 1. The test results are given in the Table hereinbelow.

EXAMPLE 13

A preparation according to the present invention having the following composition, % by mass, is formulated:

0,0-dimethyl-(2,2,2-trichloro-1-oxyethyl)phosphonate: 2.0
cetyl alcohol: 10.0
5% solution of polyvinylbutyral and resol-type phenol-formaldehyde resin (in the ratio of 1:20) in ethanol: 25.0
erythromycin: 0.4
ethanol: the balance.

The manufacture and testing of the resulting preparation are carried out as in Example 1. The test results are shown in the Table hereinbelow.

EXAMPLE 14

A preparation according to the present invention having the following composition, % by mass, is formulated:

0,0-dimethyl-(2,2,2-trichloro-1-oxyethyl)phosphonate: 2.0
dibutylphthalate: 10.0
10% solution of polyvinylbutyral and resol-type phenolformaldehyde resin (in the ratio of 1:20) in ethanol: 25.0
erythromycin: 0.4
ethanol: the balance.

The manufacture and testing of the resulting preparation are carried out similarly to those described in Example 1. The test results are shown in the Table hereinbelow.

EXAMPLE 15

A preparation according to the present invention having the following composition, % by mass, is formulated:

0,0-dimethyl-0-[1-methyl-2-(phenylcarboethoxin)-vinyl]phosphate: 2.0
castor oil: 10.0
5% solution of polyvinylbutyral and resol-type phenol-formaldehyde resin (in the ratio of 1:20) in ethanol: 25.0
isopropanol: the balance.

The manufacture and testing of the resulting preparation are carried out as in Example 1 hereinbefore. The test results are shown in the Table hereinbelow.

EXAMPLE 16

A preparation according to the present invention having the following composition, % by mass, is formulated:

0,0-dimethyl-0-[1-methyl-2(phenylcarboethoxin)vinyl]-phosphate: 2.0
birch tar: 10.0
10% solution of polyvinylbutyral and resol-type phenolformaldehyde resin (in the ratio of 1:20) in ethanol: 25.0
erythromycin: 0.4
isopropanol: the balance.

The manufacture and testing of the resulting preparation are conducted in a manner similar to that described in Example 1 hereinbefore. The test results are shown in the Table hereinbelow:

EXAMPLE 17

A preparation according to the present invention having the following composition, % by mass, is formulated:

0,0-dimethyl-0-[1-methyl-2-(phenylcarboethoxin)-vinyl]-phosphate: 2.0
cetyl alcohol: 10.0
10% solution of polyvinylbutyral and resol-type phenolformaldehyde resin (in the ratio of 1:20) in ethanol: 25.0
erythromycin: 0.4
isopropanol: the balance.

The manufacture and testing of the preparation according to the present invention are coducted as described in Example 1. The test results are give in the Table hereinbelow.

EXAMPLE 18

A preparation according to the present invention having the following composition, % by mass, is formulated:

0,0-dimethyl-0-[1-methyl-2-(phenylcarboethoxin)-vinyl]-phosphate 2.0
dibutylphthalate: 10.0
5% solution of polyvinylbutyral and resol-type phenol-formaldehyde resin (in the ratio of 1:20) in ethanol: 25.0
erythromycin: 0.4
isopropanol: the balance.

The manufacture and testing of the resulting preparation are carried out in a manner similar to that described in Example 1 hereinbefore. The test results are shown in the Table hereinbelow.

EXAMPLE 19

A preparation according to the present invention having the following composition, % by mass, is formulated:

0,0-dimethyl-(2,2,2-trichloro-1-hydroxyethyl)phosphonate: 2.0
castor oil: 10.0
5% solution of polyvinylbutyral and resol-type phenolformaldehyde resin (in the ratio of 1:20) in ethanol: 25.0
erythromycin: 0.4
isopropanol: the balance.

The manufacture and testing of the preparation according to the present invention are carried out similarly to those described in Example 1. The test results are shown in the Table hereinbelow.

EXAMPLE 20

A preparation according to the present invention having the following composition, % by mass, is formulated:

0,0-dimethyl-(2,2,2-trichloro-1-oxyethyl)phosphonate: 2.0
birch tar: 10.0
10% solution of polyvinylbutyral and resol-type phenolformaldehyde resin (in the ratio of 1:20) in ethanol: 25.0
erythromycin: 0.4
isopropanol: the balance.

The manufacture and testing of the resulting preparation are carried out as described in Example 1. The test results are shown in the Table hereinbelow.

EXAMPLE 21

A preparation according to the present invention having the following composition, % by mass, is formulated:

0,0-dimethyl-(2,2,2-trichloro-1-oxyethyl)phosphonate: 2.0
cetyl alcohol: 10.0
5% solution of polyvinylbutyral and resol-type phenolformaldehyde resin (in the ratio of 1:20) in ethanol: 25.0
erythromycin: 0.4
isopropanol: the balance.

The manufacture and testing of the resulting preparation are carried out as described in Example 1. The test results are shown in the Table hereinbelow.

EXAMPLE 22

A preparation according to the present invention having the following composition, % by mass, is formulated:

0,0-dimethyl-(2,2,2-trichloro-1-oxyethyl)phosphonate: 2.0
dibutylphthalate: 10.0
10% solution of polyvinylbutyral and resol-type phenolformaldehyde resin (in the ratio of 1:20) in ethanol: 25.0
erythromycin: 0.4
isopropanol: the balance.

The manufacture and testing of the preparation are similar to those described in Example 1 hereinbefore. The test results are shown in the Table hereinbelow.

EXAMPLE 23

A preparation according to the present invention having the following composition, % by mass, is formulated:

0,0-dimethyl-0-[1-methyl-2-(phenylcarboethoxin)-vinyl]-phosphate: 2.0
castor oil: 10.0
5% solution of polyvinylbutyral and resol-type phenolformaldehyde resin (in the ratio of 1:20) in ethanol: 25.0
erythromycin: 0.4
ethylacetate: the balance.

The manufacture and testing of the preparation thus produced are carried out as in Example 1. The results of the tests are shown in the Table hereinbelow.

EXAMPLE 24

A preparation according to the present invention having the following composition, % by mass, is formulated:

0,0-dimethyl-0-[1-methyl-2-(phenylcarboethoxin)-vinyl]-phosphate: 2.0
birch tar: 10.0
10% solution of polyvinylbutyral and resol-type phenolformaldehyde resin (in the ratio of 1:20) in ethanol: 25.0
erythromycin: 0.4
ethylacetate: the balance.

The manufacture and testing of the resulting preparation are conducted in a manner similar to that described in Example 1. The test results are shown in the Table hereinbelow.

EXAMPLE 25

A preparation according to the present invention having the following composition, % by mass, is formulated:

0,0-dimethyl-0-[1-methyl-2(phenylcarboethoxin)vinyl]-phosphate: 2.0
cetyl alcohol: 10.0
5% solution of polyvinylbutyral and resol-type phenolformaldehyde resin (in the ratio of 1:20) in ethanol: 25.0
erythromycin: 0.4
ethylacetate: the balance.

The manufacture and testing of the resulting preparation are conducted as described in Example 1 hereinbefore. The test results are shown in the Table hereinbelow.

EXAMPLE 26

A preparation according to the present invention having the following composition, % by mass, is formulated:

0,0-dimethyl-0-[1-methyl-2(phenylcarboethoxin)vinyl]-phosphate: 2.0
dibutylphthalate: 10.0
10% solution of polyvinylbutyral and resol-type phenolformaldehyde resin (in the ratio of 1:20) in ethanol: 25.0
erythromycin: 0.4
ethylacetate: the balance.

The manufacture and testing of the resulting preparation are carried out as in Example 1. The test results are shown in the Table hereinbelow.

EXAMPLE 27

A preparation according to the present invention having the following composition, percent by mass, is formulated:
0,0-dimethyl-(2,2,2-trichloro-1-oxyethyl)phosphonate: 2.0
castor oil: 10.0
10% solution of polyvinylbutyral and resol-type phenolformaldehyde resin in ethanol (in the ratio of 1:20): 25.0
erythromycin: 0.4
ethylacetate: the balance.

The manufacture and testing of the resulting preparation are conducted in a manner similar to that described in the foregoing Example 1. The test results are shown in the Table hereinbelow.

EXAMPLE 28

A preparation according to the present invention having the following composition, % by mass, is formulated:
0,0-dimethyl-(2,2,2-trichloro-1-oxyethyl)phosphonate: 2.0
birch tar: 10.0
5% solution of polyvinylbutyral and resol-type phenolformaldehyde resin (in the ratio of 1:20) in ethanol: 25.0
erythromycin: 0.4
ethylacetate: the balance.

The manufacture and testing of the preparation thus obtained are carried out as described in Example 1. The test results are given in the Table hereinbelow.

EXAMPLE 29

A preparation of the following composition, percent by mass, is formulated according to the present invention:
0,0-dimethyl-(2,2,2-trichloro-1-oxyethyl)phosphonate: 2.0
cetyl alcohol: 10.0
10% solution of polyvinylbutyral and resol-type phenolformaldehyde resin (in the ratio of 1:20) in ethanol: 25.0
erythromycin: 0.4
ethylacetate: the balance.

The manufacture and testing of the preparation are carried out as described in Example 1 hereinbefore. The test results are shown in the Table hereinbelow.

EXAMPLE 30

A preparation according to the present invention having the following composition, % by mass, is formulated:
0,0-dimethyl-(2,2,2-trichloro-1-hydroxyethyl)-phosphonate: 2.0
dibutylphthalate: 10.0
5% solution of polyvinylbutyral and resol-type phenolformaldehyde resin (in the ratio of 1:20) in ethanol: 25.0
erythromycin: 0.4
ethylacetate: the balance.

The manufacture and testing of the resulting preparation are conducted in a manner similar to that described in Example 1. The test results are shown in the Table hereinbelow.

EXAMPLE 31

A preparation according to the present invention having the following composition, % by mass, in formulated:
0,0-dimethyl-0-[1-methyl-2(phenylcarboethoxin)vinyl]-phosphate: 2.0
castor oil: 10.0
5% solution of polyvinylbutyral and resol-type phenolformaldehyde resin (in the ratio of 1:20) in ethanol: 25.0
erythromycin: 0.4
prednizone: 0.03
ethanol: the balance.

The manufacture and testing of the preparation according to the present invention are carried out as described in Example 1. The test results are shown in the Table hereinbelow.

EXAMPLE 32

A preparation according to the present invention having the following composition, % by mass, is formulated:
0,0-dimethyl-(2,2,2-trichloro-1oxyethyl)phosphonate: 2.0
castor oil: 10.0
5% solution of polyvinylbutyral and resol-type phenolformaldehyde resin (in the ratio of 1:20) in ethanol: 25.0
erythromycin: 0.4
prednizone: 0.03
ethanol: the balance.

The manufacture and testing of the preparation according to the present invention are carried out as in Example 1 hereinbefore. The test results are presented in the Table hereinbelow.

EXAMPLE 33

A preparation according to the present invention having the following composition, % by mass, is formulated:
0,0-dimethyl-0-[1-methyl-2(phenylcarboethoxin)vinyl]-phosphate: 2.0
birch tar: 10.0
5% solution of polyvinylbutyral and resol-type phenolformaldehyde resin (in the ratio of 1:20) in ethanol: 25.0
erythromycin: 0.4
prednizone: 0.03
ethanol: the balance.

The manufacture and testing of the preparation according to the present invention are carried out as in Example 1. The test results are shown in the Table hereinbelow.

EXAMPLE 34

A preparation according to the present invention having the following composition, % by mass, is formulated:
0,0-dimethyl-(2,2,2-trichloro-1-oxyethyl)phosphonate: 2.0
birch tar: 10.0
10% solution of polyvinylbutyral and resol-type phenolformaldehyde resin (in the ratio of 1:20) in ethanol: 25.0
erythromycin: 0.4
prednizone: 0.03
ethanol: the balance.

The preparation thus obtained is manufactured and tested as described in Example 1. The test results are shown in the Table hereinbelow.

EXAMPLE 35

A preparation according to the present invention having the following composition, % by mass, is formulated:
0,0-dimethyl-[1-methyl-2-(phenylcarboethoxin)vinyl]-phosphate: 2.0
cetyl alcohol: 10.0
10% solution of polyvinylbutyral and resol-type phenolformaldehyde resin (in the ratio of 1:20) in ethanol: 25.0
erythromycin: 0.4
prednizone: 0.03
ethanol: the balance.

The manufacture and testing of the resulting preparation are carried out as described in Example 1. The test results are given in the Table hereinbelow.

EXAMPLE 36

A preparation according to the present invention having the following composition, % by mass, is formulated:
0,0-dimethyl-(2,2,2-trichloro-1-oxyethyl)phosphonate: 2.0
cetyl alcohol: 10.0
5% solution of polyvinylbutyral and resol-type phenolformaldehyde resin (in the ratio of 1:20) in ethanol: 25.0
erythromycin: 0.4
prednizone: 0.03
ethanol: the balance.

The manufacture and testing of the preparation are carried out as in Example 1 hereinbefore. The test results are shown in the Table hereinbelow.

EXAMPLE 37

A preparation according to the present invention having the following composition, % by mass, is formulated:
0,0-dimethyl-0-[1-methyl-2(phenylcarboethoxin)vinyl]-phosphate: 2.0
dibutylphthalate: 10.0
5% solution of polyvinylbutyral and resol-type phenolformaldehyde resin (in the ratio of 1:20) in ethanol: 25.0
erythromycin: 0.4
prednizone: 0.03
ethanol: the balance.

The manufacture and testing of the preparation are carried out as described in Example 1. The test results are shown in the Table hereinbelow.

EXAMPLE 38

A preparation according to the present invention having the following composition, % by mass, is formulated:
0,0dimethyl-(2,2,2-trifluoro-1-oxyethyl) phosphonate: 2.0
dibutylphthalate: 10.0
10% solution of polyvinylbutyral and resol-type phenolformaldehyde resin (in the ratio of 1:20) in ethanol: 25.0
erythromycin: 0.4
prednizone: 0.03
ethanol: the balance.

The manufacture and testing of the preparation are carried out as in Example 1 hereinbefore. The test results are shown in the Table hereinbelow.

EXAMPLE 39

A preparation according to the present invention having the following composition, % by mass: is formulated:
0,0-dimethyl-0-[1-methyl-2(phenylcarboethoxin)vinyl]-phosphate: 2.0
castor oil: 10.0
5% solution of polyvinylbutyral and resol-type phenolformaldehyde resin (in the ratio of 1:20) in ethanol: 25.0
erythromycin: 0.4
prednizone: 0.03
isopropanol: the balance.

The manufacture and testing of the resulting preparation are carried out in a manner similar to that described in Example 1. The test results are shown in the Table hereinbelow.

EXAMPLE 40

A preparation according to the present invention having the following composition, % by mass, is formulated:
0,0-dimethyl-0-[1-methyl-2(phenylcarboethoxin)vinyl]-phosphate: 2.0
birch tar: 10.0
5% solution of polyvinylbutyral and resol-type phenolformaldehyde resin (in the ratio of 1:20) in ethanol: 25.0
erythromycin: 0.4
prednizone: 0.03
ethylacetate: the balance.

The manufacture and testing of the resulting preparation are carried out as described in Example 1. The test results are given in the Table hereinbelow.

EXAMPLE 41

A preparation according to the present invention having the following composition, % by mass, is formulated:
0,0-dimethyl-0-[1-methyl-2(phenylcarboethoxin)]-phosphate: 2.0
cetyl alcohol: 10.0
10% solution of polyvinylbutyral and resol-type phenolformaldehyde resin (in the ratio of 1:20) in ethanol: 25.0
erythromycin: 0.4
prednizione: 0.03
ethylacetate: the balance.

The manufacture and testing of the resulting preparation are carried out as described in Example 1. The test results are given in the Table hereinbelow.

EXAMPLE 42

A preparation according to the present invention having the following composition, % by mass, is formulated:
0,0-dimethyl-0-[1-methyl-2(phenylcarboethoxin)vinyl]-phosphate: 2.0
dibutylphthalate: 10.0
5% solution of polyvinylbutyral and resol-type phenolformaldehyde resin (in the ratio of 1:20) in ethanol: 25.0
erythromycin: 0.4
prednizone: 0.03 isopropanol: the balance.

The manufacture and testing of the preparation are carried out in a manner similar to that described in Example 1. The test results are shown in the Table hereinbelow.

EXAMPLE 43

A preparation according to the present invention having the following composition, % by mass, is formulated:
0,0-dimethyl-0-[1-methyl-2(phenylcarboethoxin)vinyl]-phosphate: 2.0
castor oil: 10.0
5% solution of polyvinylbutyral and resol-type phenol-formaldehyde resin (in the ratio of 1:20) in ethanol: 25.0
erythromycin 0.4
prednizione 0.03
difluorodichloroethane 10.0
ethanol the balance.

The manufacture and testing of the resulting preparation are carried out as in Example 1 hereinbefore. The test results are given in the Table hereinbelow.

EXAMPLE 44

A preparation of the present invention having the following composition, % by mass, is formulated:
0,0-dimethyl-0-[1-methyl-2(phenylcarboethoxin)vinyl]-phosphate: 2.0
castor oil: 10.0
5% solution of polyvinylbutyral and resol-type phenol-formaldehyde resin (in the ratio of 1:20) in ethanol: 25.0
erythromycin: 0.4
prednizione: 0.03
mixture of difluorodichloroethane with propanebutane: 10.0
ethanol: the balance.

The manufacture and testing of the resulting preparation are carried out as described in Example 1. The test results are given in the Table hereinbelow.

EXAMPLE 45

A preparation according to the present invention having the following composition, % by mass, is formulated:
0,0-dimethyl-0-[1-methyl-2(phenylcarboethoxin)vinyl]-phosphate: 2.0
birch tar: 10.0
5% solution of polyvinylbutyral and resol-type phenol-formaldehyde resin (in the ratio of 1:20) in ethanol: 25.0
difluorodichloroethane: 40.0
erythromycin: 0.4
ethanol: the balance.

The manufacture and testing of the resulting preparation are carried out as described in Example 1 hereinbefore. The test results are shown in the Table hereinbelow.

EXAMPLE 46

A preparation according to the present invention having the following composition, % by mass, is formulated:
0,0-dimethyl-(2,2,2-trichloro-1-oxyethyl)phosphonate: 2.0
birch tar: 10.0
5% solution of polyvinylbutyral and resol-type phenol-formaldehyde resin (in the ratio of 1:20) in ethanol: 25.0
erythromycin: 0.4
prednizione: 0.03
mixture of difluorodichloroethane with propanebutane: 10.0
ethanol: the balance.

The manufacture and testing of the resulting preparation are carried out as described in Example 1. The test results are shown in the Table hereinbelow.

EXAMPLE 47

A preparation according to the present invention having the following composition, percent by mass, is formulated:
0,0-dimethyl-(2,2,2-trichloro-1-oxyethyl)phosphonate: 2.0
cetyl alcohol: 10.0
5% solution of polyvinylbutyral and resol-type phenol-formaldehyde resin (in the ratio of 1:20) in ethanol: 25.0
erythromycin: 0.4
mixture of difluorodichloroethane with propanebutane: 40.0
ethylacetate: the balance.

The manufacture and testing of the resulting preparation are carried out in a manner similar to that described in the foregoing Example 1. The test results are shown in the Table hereinbelow.

TABLE

Results of testing the preparation of the present invention and the known preparation

| The preparation according to the invention, Example No 1 | Duration of the film coating service life, days 2 | Healing period of wounds, days 3 | Larvicidal effect of the preparation of this invention and of the known preparation 4 |
|---|---|---|---|
| No. 1 | 10 | 6 | 100% death of larvae, no repeated invasion |
| No. 2 | 10 | 6 | 100% death of larvae, no repeated invasion |
| No. 3 | 7 | 7 | 100% death of larvae, no repeated invasion |
| No. 4 | 10 | 6 | 100% death of larvae, no repeated invasion |
| No. 5 | 10 | 6 | 100% death of larvae, no repeated invasion |
| No. 6 | 7 | 7 | 100% death of larvae, no repeated invasion |
| No. 7 | 7 | 7 | 100% death of larvae, no repeated invasion |
| No. 8 | 7 | 7 | 100% death of larvae, no repeated invasion |
| No. 9 | 10 | 6 | 100% death of larvae, no repeated |

TABLE-continued

Results of testing the preparation of the present invention and the known preparation

| The preparation according to the invention, Example No 1 | Duration of the film coating service life, days 2 | Healing period of wounds, days 3 | Larvicidal effect of the preparation of this invention and of the known preparation 4 |
|---|---|---|---|
| No. 10 | 9 | 6 | 100% death of larvae, no repeated invasion |
| No. 11 | 8 | 7 | 100% death of larvae, no repeated invasion |
| No. 12 | 8 | 7 | 100% death of larvae, no repeated invasion |
| No. 13 | 7 | 7 | 100% death of larvae, no repeated invasion |
| No. 14 | 8 | 6 | 100% death of larvae, no repeated invasion |
| No. 15 | 8 | 7 | 100% death of larvae, no repeated invasion |
| No. 16 | 8 | 7 | 100% death of larvae, no repeated invasion |
| No. 17 | 7 | 7 | 100% death of larvae, no repeated invasion |
| No. 18 | 7 | 7 | 100% death of larvae, no repeated invasion |
| No. 19 | 8 | 7 | 100% death of larvae, no repeated invasion |
| No. 20 | 10 | 6 | 100% death of larvae, no repeated invasion |
| No. 21 | 8 | 7 | 100% death of larvae, no repeated invasion |
| No. 22 | 8 | 7 | 100% death of larvae, no repeated invasion |
| No. 23 | 7 | 7 | 100% death of larvae, no repeated invasion |
| No. 24 | 9 | 6 | 100% death of larvae, no repeated invasion |
| No. 25 | 8 | 7 | 100% death of larvae, no repeated invasion |
| No. 26 | 7 | 7 | 100% death of larvae, no repeated invasion |
| No. 27 | 7 | 7 | 100% death of larvae, no repeated invasion |
| No. 28 | 9 | 6 | 100% death of larvae, no repeated invasion |
| No. 29 | 7 | 7 | 100% death of larvae, no repeated invasion |
| No. 30 | 7 | 7 | 100% death of larvae, no repeated invasion |
| No. 31 | 7 | 7 | 100% death of larvae, no repeated invasion |
| No. 32 | 8 | 7 | 100% death of larvae, no repeated invasion |
| No. 33 | 10 | 6 | 100% death of larvae, no repeated invasion |
| No. 34 | 10 | 6 | 100% death of larvae, no repeated invasion |
| No. 35 | 7 | 7 | 100% death of larvae, no repeated invasion |
| No. 36 | 7 | 7 | 100% death of larvae, no repeated invasion |
| No. 37 | 7 | 7 | 100% death of larvae, no repeated invasion |
| No. 38 | 7 | 7 | 100% death of larvae, no repeated invasion |
| No. 39 | 8 | 7 | 100% death of larvae, no repeated invasion |
| No. 40 | 8 | 7 | 100% death of larvae, no repeated invasion |
| No. 41 | 10 | 6 | 100% death of larvae, no repeated invasion |
| No. 42 | 8 | 7 | 100% death of larvae, no repeated invasion |
| No. 43 | 8 | 7 | 100% death of larvae, no repeated invasion |
| No. 44 | 8 | 7 | 100% death of larvae, no repeated invasion |
| No. 45 | 9 | 7 | 100% death of larvae, no repeated |

TABLE-continued

Results of testing the preparation of the present invention and the known preparation

| The preparation according to the invention, Example No 1 | Duration of the film coating service life, days 2 | Healing period of wounds, days 3 | Larvicidal effect of the preparation of this invention and of the known preparation 4 |
|---|---|---|---|
| No. 46 | 10 | 6 | invasion 100% death of larvae, no repeated invasion |
| No. 47 | 9 | 7 | 100% death of larvae, no repeated invasion |
| Control, single | — | no healing of the treated animals, since a repeated invasion is observed on the 3-rd day | Within 2-3 days the larvacidal effect disappears in 95% of the treated animals |
| Control, double | — | no healing in 25% of the treated animals, since a repeated invasion is observed on the 3-d day | Within 2-3 days the larvacidal effect disappears in 95% of the treated animals |

EXAMPLE 48

A flock of 60 sheep heads selected by the principle of analogs was formed for carrying out experiments for evaluation of the efficiency of the preparation according to the present invention having the following composition, % by mass:

0,0-dimethyl-0-[1-methyl-2-(phenylcarboethoxin)-vinyl]-phosphate: 1.4
birch tar: 1.0
10% solution of polyvinyl butyral and resol resin in ethanol: 16.0
erythromycin: 0.1
ethanol: the balance.

After shearing in all animals wounds were made in the external surface of thigh zone with the area of 10 cm$^2$. An experiment for determination of a preventive efficiency was carried out with 20 sheep heads. Wounds of 10 sheeps were treated by the preparation according to the present invention, while the remaining animals were treated by the method of spraying with a 3% aqueous solution of 0,0-dimethyl-(2,2,2-trichloro-1-hydroxyethyl)-phosphonate. The wounds treated with these preparations were subjected to a daily inspection. As a result of the examination it has been found that on the surface of wounds treated with the preparation according to the present invention directly after the treatment a film coating is formed which is resistant to mechanical injuries and reliably protects wounds from infection with myiases and pyogenic microflora. The wound healing under the film took place within 6-7 days. The protective effect of a 9% solution of 0,0-dimethyl-(2,2,2-trichloro-1-oxyethyl)-phosphonate was observed for 3 days, whereafter larvae of myiasic flies were noted in 8 wounds out of 10 which necessitated a repeated spraying of the wounds with the same solution. On the 7-th day of the experiment the wounds of this group of sheeps were once more sprayed with this solution. The healing of the wounds was recorded on the 10-12-th day. After 4 days since scarification of the animals' skin 20 heads of sheep were chosen which had larvae of myasic flies in the wounds. Out of them 2 groups were formed of 10 heads in each. The animals' wounds in the first group were treated with the preparation according to the present invention and the second group of animals was dipped in a 1% solution of 0,0-dimethyl-(2,2,2-trichloro-1-oxyethyl)-phosphonate.

After treatment with the preparation according to the present invention there was observed a random movement of the larvae in the wound. A major portion of the larvae fell out of the wound and died within 20 minutes. The remaining larvae that left the sites of their parasitism were coated with the film-forming composition and died on the wound surface.

The death of larvae of myiasic flies in wounds of the sheep dipped in a 1% solution of 0,0-dimethyl-(2,2,2-trichloro-1-oxyethyl)-phosphonate took place within 60-90 minutes after the dipping. An insignificant portion of the larvae was washed out of the wounds at the moment of dipping, the remaining larvae died without leaving the sites of parasitism which necessitated cleaning of the wounds in order to avoid a purulent decay of tissues of the dead larvae and infecting of the wounds. The observation over the wound condition was conducted on a daily basis for the period of 15 days. It was found that on the surface of wounds treated with the preparation according to the present invention a water-insoluble vapour-permeable film was formed which was resistant to mechanical damages. On its surface there were inclusions in the form of mummified larvae of the first age. The film retained on the wound surface for 9-10 days; the wound healing was observed on the 6-7-th day. On the third day after dipping of the group of sheeps in the above-specified solution a repeated invading of the wounds with larvae of myiasic flies was observed, whereafter the dipping was performed once more. The overall number of dippings during the treatment period till a complete healing of the wounds, i.e. over 12 days, was three.

What is claimed is:

1. A preparation for prophylaxis and treatment of myiases of animals comprising the following components, % by mass:

an insecticide exhibiting a larvicidal effect: 1.4 to 2.3
a 5-20% solution, in ethanol, of polyvinylbutyral and a resoltype phenolformaldehyde resin taken in a ratio of 1:10-45: 16.0 to 35.0
a plastifying agent improving elasticity of the formed polymeric film: 1.0 to 20.0
an antibiotic: 0.1 to 0.7
an organic solvent: the balance.

2. A preparation as claimed in claim 1, wherein as the insecticide possessing a larvicidal effect an insecticide is used which is selected from the group consisting of 0,0-dimethyl-0-[1-methyl-2(phenylcarboethoxin)vinyl]-phosphate and 0,0-dimethyl-(2,2,2-trichloro-1-oxyethyl)phosphonate.

3. A preparation as claimed in claim 1, wherein as the plastifying agent improving elasticity of the formed polymeric film a plastifier is contained which is selected from the group consisting of castor oil and birch tar.

4. A preparation as claimed in claim 1, wherein as the antibiotic erythromycin is used.

5. A preparation as claimed in claim 1, wherein as the organic solvent a solvent is contained which is selected from the group consisting of ethylacetate, ethanol and isopropanol.

6. A preparation as claimed in claim 1, wherein a propellent is additionally contained in an amount of 10–40% by mass.

7. A preparation as claimed in claim 6, wherein as the propellent a propellent is contained which is selected from the group consisting of difluorodichloromethane and a mixture of difluorodichloromethane with propanebutane.

8. A preparation as claimed in claim 1, wherein prednizone is additionally contained in an amount of from 0.02 to 0.04% by mass.

* * * * *

UNITED STATES PATENT AND TRADEMARK OFFICE
CERTIFICATE OF CORRECTION

PATENT NO. : 4,731,240

DATED : March 15, 1988

INVENTOR(S) : Alexandr Andreevich Zakomyrdin et al

It is certified that error appears in the above-identified patent and that said Letters Patent is hereby corrected as shown below:

On the title page, the following should be inserted:

-- (73) Assignee: Vsesojuzny Nauchno-Issledovatelsky Institut Veterinarnoi Sanitarii --

Signed and Sealed this

First Day of November, 1988

Attest:

DONALD J. QUIGG

*Attesting Officer*         *Commissioner of Patents and Trademarks*